US012188071B1

(12) United States Patent
Ho et al.

(10) Patent No.: US 12,188,071 B1
(45) Date of Patent: Jan. 7, 2025

(54) CHITOSAN COMPOSITION AND METHOD OF MANUFACTURING THE SAME

(71) Applicant: Vien Anh Xuan Ho, Ho Chi Minh (VN)

(72) Inventors: Vien Anh Xuan Ho, Ho Chi Minh (VN); My Anh Xuan Ho, Ho Chi Minh (VN); Huy Vu Thanh Nguyen, Ho Chi Minh (VN); Huy Vo Thanh Nguyen, Ho Chi Minh (VN)

(73) Assignee: Vien Anh Xuan Ho, Ho Chi Minh (VN)

( * ) Notice: Subject to any disclaimer, the term of this patent is extended or adjusted under 35 U.S.C. 154(b) by 0 days.

(21) Appl. No.: 18/818,636

(22) Filed: Aug. 29, 2024

Related U.S. Application Data

(63) Continuation-in-part of application No. 18/592,551, filed on Mar. 1, 2024, now Pat. No. 12,042,521.

(51) Int. Cl.
*A61K 36/07* (2006.01)
*C12N 1/14* (2006.01)
*C12N 1/20* (2006.01)
*C12P 19/04* (2006.01)
*C12R 1/02* (2006.01)
*C12R 1/07* (2006.01)
*C12R 1/225* (2006.01)

(52) U.S. Cl.
CPC ............... *C12P 19/04* (2013.01); *C12N 1/14* (2013.01); *C12N 1/20* (2013.01); *C12R 2001/02* (2021.05); *C12R 2001/07* (2021.05); *C12R 2001/225* (2021.05)

(58) Field of Classification Search
None
See application file for complete search history.

*Primary Examiner* — Russell G Fiebig

(57) ABSTRACT

A method of manufacturing a chitosan composition comprising steps performed in the following specific order: (i) preparing materials; (ii) creating a chitin ingredient from shrimp shells; (iii) creating a chitin ingredient from oyster mushroom; (iv) creating a chitin mixture by homogenously mixing the chitin ingredient from shrimp shells with the chitin ingredient from oyster mushroom; (v) loading the chitin mixture into the centrifugal spray drying device having predetermined specifications to create the chitosan composition; and (vi) packaging and preservation.

20 Claims, 3 Drawing Sheets

CHITOSAN COMPOSITION AND METHOD OF MANUFACTURING THE SAME

CLAIM OF PRIORITY

This application is a continuation application of application Ser. No. 18/592,551, entitled "A method for producing a complex composition of turkey tail mushroom extract-chitosan", filed on Mar. 1, 2024. The patent application identified above is incorporated here by reference in its entirety to provide continuity of disclosure.

FIELD OF THE INVENTION

The present invention relates to a chitosan composition and method of manufacturing the same.

BACKGROUND ART

Chitin is a natural high molecular weight polymer widely found in nature. It is the main component of insect and crustacean cuticle, and is also part of the cell walls of some fungi and other organisms. Chitin is generally extracted from its natural sources by treatments with strong acid (to remove calcium deposits where required) and strong alkali (to remove proteinaceous residue). Chitin is insoluble under typical aqueous conditions and is considered to be a relatively intractable polymer (difficult to process). Dissolution of chitin to enable direct processing into fibers or other forms requires the use of unattractive solvent systems that are generally corrosive and toxic.

Fisheries is one of Vietnam's key economic sectors, bringing a large source of foreign exchange revenue to the country. In 2022, seafood export turnover will reach 11 billion USD, of which shrimp is the object with the highest export value reaching 4.1-4.2 billion USD. Currently, the intensive shrimp farming model is deployed and brings high economic efficiency in many localities across the country. Good control of environmental conditions in this farming model helps reduce the risk of disease for shrimp. However, due to the high density of shrimp, a large amount of waste during the farming process including leftover food, feces, suspended matter, molting shells of shrimp . . . has the potential to pollute the water environment, causing outbreaks, shrimp disease. In particular, a large amount of molting shells of shrimp can be obtained by siphoning every day. Taking advantage of this source of molted shells as a raw material to produce chitin and chitosan not only adds value to farmed shrimp, but also reduces pollution of the farming environment, improving value for the shrimp farming, processing and export chain, contributing to sustainable development of the fisheries industry.

In addition, refer to Table 1, survey results on the differences in physical, chemical and biological characteristics between molting shell of shrimp and shrimp shells wasted from seafood processing. This is also one of the reasons for choosing molting shell of shrimp as a potential raw material source that can be researched to be used as raw materials for chitin and chitosan production, aims to solve the current problem of shortage of raw materials to produce chitin and chitosan.

TABLE 1

Compare features physical, chemical and biological characteristics between molting shell of shrimp and shrimp shells wasted from seafood processing

| Characteristics | Molting shell of shrimp | Shrimp shells wasted from seafood processing |
|---|---|---|
| Physical | Soft and thin | Hard and thick |
| Chemical | High mineral content due to the process of mineral accumulation in the shell before molting and in an amorphous state with alternating layers of chitin, chitin-binding proteins in the cuticle are also calcified (including in the head and body shells), contains little protein and astaxanthin | Chitin is strongly bound to proteins and minerals, contains astaxanthin, high protein content in the epidermis, especially highly concentrated in the composition of shrimp heads (meat and organs) |
| Biological | Contains chitinase enzyme | Contains chitinase enzyme, but quickly goes rancid due to its high protein content |

In recent years, the industrialized production of edible mushroom such as *Pleurotus pulmonarius, Pleurotus* cf. *floridanus, Pleurotus ostreatus*, and *Pleurotus citrinopileatus* is rapidly developed, and the production of chitin by using non-traditional resources such as mushroom is gradually increased. Besides, the waste edible mushroom accounts for about 20% of the total yield of the edible mushroom, and provides the possibility for extracting chitin from the waste edible mushroom. Biological fermentation technology is an emerging technology and is widely applied to extraction of mushroom chitosan. However, the liquid fermentation of the fungus mycelium is directly carried out to extract chitosan from the fungus mycelium, and the problems of high equipment requirement, strict control of culture medium and culture conditions, high input cost, low product purity and the like exist.

The antibacterial activity test also showed that the bacteriostatic effect gradually increased with the decrease of the relative molecular mass of the water-soluble chitosan, especially when the relative molecular mass was about 1500. Comparative experiments have also shown that the presence of free amino groups is the basis for the antibacterial action of water-soluble chitosan. Because the positive charge of the water-soluble chitosan and its polymeric molecular structure can adsorb and aggregate with the flagella and the membrane on the surface of the pathogen, thereby inhibiting the proliferation of pathogenic bacteria.

The preparation methods of water-soluble chitosan mainly include chemical degradation method, physical degradation method and enzymatic degradation method. The chemical degradation method is divided into acid hydrolysis method and oxidation method. The acid hydrolysis method is the earliest chitosan degradation method. As early as the 1950s, detailed research was carried out. Plus, other processes such as acetic acid method, concentrated sulfuric acid method and hydrofluoric acid method appeared. However, these methods all have environmental pollution, and the reaction end point should not be controlled. Hydrogen peroxide oxidation is representative, mainly $H_2O_2$, $H_2O_2$-HCL, $ClO_2$ method, etc., and the disadvantage is that it is easy to produce by-products.

Enzymatic hydrolysis is the use of specific chitosanase and other non-specific enzymes, such as chitinase, cellulase, lipase and other chitosan degradation, can be used for enzymatic hydrolysis of various enzymes More than 30 kinds. Enzymatic degradation is generally superior to chemical degradation. It is carried out under milder reaction conditions. Compared to the other two methods, the enzymatic degradation method does not require the addition of a large amount of reagents and is less polluting to the environment. The specific enzyme mainly specifically cleaves the β-1,4-glycosidic bond of chitosan to achieve the purpose of degradation. No other reagents are added during the whole degradation process, no other reaction by-products are formed, which is chitosan degradation. The most ideal method, but currently the specific chitosan degrading enzyme has less source, low activity and high preparation cost. Non-specific enzymatic hydrolysis has been studied by many people, such as Jiangnan University using wheat germ lipase for degradation. Water-soluble chitosan with a homopolymeric molecular weight of tens of thousands. In addition, cellulase, papain, and glucanase are used to degrade chitosan, but the degradation efficiency is not high, and lower molecular weight cannot be obtained. Water-soluble chitosan, such as cellulase degradation by cellulase, requires about 10% of the substrate. When degraded with protease, only 40% of chitosan can be converted. Production using non-specific enzymes alone is not competitive in terms of product cost.

The physical method is mainly ultrasonic, microwave, electromagnetic wave radiation degradation method, among which the research on ultrasonic degradation method is more, and the degradation of chitosan is caused by the breakage of chemical bonds in the molecule during the radiation process. However, the degradation of water-soluble chitosan by physical degradation is limited by the degradation mechanism. The polymerization chain of chitosan is broken at random during the degradation process. The average molecular weight distribution of the product is too wide, and it is difficult to obtain a product with a molecular weight below 40,000. The low content of water-soluble chitosan of 6-8 leads to a large waste of raw materials, which greatly limits the application of physical methods.

Therefore, it is necessary to have a method of manufacturing the chitosan composition combined with chemical treatment and biological enzymatic treatment for taking its essence, to its shortcomings.

Furthermore, what is needed to have a method of manufacturing the chitosan composition using combined raw materials including the molting shell of shrimp, and oyster mushrooms.

Finally, what is needed to provide a method of manufacturing the chitosan composition is capable of dissolving in water, a pH of 7-8.5, which is economical in production and relatively controllable in product quality.

This invention provides solutions to achieve the above goals.

SUMMARY OF THE INVENTION

Accordingly, an objective of the present invention is to provide a method of manufacturing a chitosan composition comprising steps performed in the following specific order:

(i) preparing materials including: a microorganism solution, a fruit vinegar, an enzyme solution, and a rice alcohol has alcohol range 30%-50%;

(ii) creating a chitin ingredient from shrimp shells;

(iii) creating a chitin ingredient from oyster mushroom;

(iv) creating a chitin mixture by homogenously mixing (1-10) parts of the chitin ingredient from shrimp shells at step (ii) with 1 part of the chitin ingredient from oyster mushroom at step (iii);

(v) loading the chitin mixture into the centrifugal spray drying device having predetermined specifications to create the chitosan composition; in which predetermined specifications include: a rotate speed of 1200 rpm for 3-5 hours at temperature 20° C.-28° C.; and (vi) packaging and preservation.

Another objective of the present invention is to provide the chitin ingredient from shrimp shells comprising performing in a specific order from (a) to (c):

(a) collecting a molting shell of shrimp, then washing to remove impurities, and soaking with HCl solution in a ratio of 1: (3-5) (w/v) for 15-20 days, then filtering to remove liquid, washing twice with the rice alcohol has alcohol range 30%-50% to obtain a first temporary mixture;

(b) treating the first temporary mixture to obtain a basic solution including:
dissolving a quicklime (CaO) ingredient in solution concentrated HCl contains 40% (concentrated grade) with combined stirring at 50 rpm for 5 minutes to obtain a solution 1;
admixing the first temporary mixture to the solution 1 with combined stirring at 50 rpm for 5 minutes, then stop stirring and let stand for 7-10 days at 28° C.-40° C. to obtain the basic solution;
wherein a ratio of the first temporary mixture and the quicklime (CaO) ingredient is 1: (2-5) (w/w);
wherein a ratio of the quicklime (CaO) ingredient and the solution concentrated HCl contains 40% (concentrated grade) is 1: (2-5) (w/v);
(c) admixing 1 part of the enzyme solution into 10 parts of the basic solution, then stop stirring and let stand for 12-18 hours to obtain the chitin ingredient from shrimp shells.

Another objective of the present invention is to provide the chitin ingredient from oyster mushroom comprising performing in a specific order from (a') to (d'):
(a') collecting oyster mushrooms, then washing to remove impurities, and soaking with a fruit vinegar in a ratio of 1: (3-5) (w/v) for 15-20 days, then filtering to remove liquid, and washing twice with the rice alcohol has alcohol range 30%-50% to obtain a second temporary mixture; wherein the fruit vinegar has a concentration of 35%-55%;
(b') treating the second temporary mixture to obtain a basic temporary solution including:
dissolving a quicklime (CaO) ingredient in solution concentrated HCl contains 40% (concentrated grade) with combined stirring at 50 rpm for 5 minutes to obtain the solution 1;
admixing the second temporary mixture to the solution 1 with combined stirring at 50 rpm for 5 minutes, then stop stirring and let stand for 7-10 days at 28° C.-40° C. to obtain the basic temporary solution;
wherein a ratio of the second temporary mixture and the quicklime (CaO) ingredient is 1: (3-5) (w/w);
wherein a ratio of the quicklime (CaO) ingredient and the solution concentrated HCl contains 40% (concentrated grade) is 1: (2-5) (w/v);
(c') admixing a microorganism solution into the basic temporary solution at a ratio of (1-2): 10 (w/v) to obtain a foundation temporary solution; and
(d') adjusting pH of the foundation temporary solution reached 6.8-7.2, then fermenting at 30° C.-40° C. for 125-135 hours to obtain the chitin temporary mixture from oyster mushroom.

Yet another objective of the present invention is to provide the fruit vinegar comprising performing in a specific order from (A') to (G'):
(A') selecting and preparing fruits by a predetermined quality guideline, includes selecting said fruits that have a Brix level of at highest 2; in which fruits are selected from the group consisting of ambarella (*Spondias dulcis*), plum (*Prunus salicina*), apricot (*Prunus armeniaca* (L.)), crocodile fruit (*Dracontomelon duperreanum*), star gooseberry (*Phyllanthus acidus* (L.)), and a combination thereof;
(B') performing visual inspection to select undamaged fruits;
(C') washing fruits, then cold-squeezing fruits to obtain a fruit juice;
(D') creating a foundation solution by mixing the fruit juice and the coconut water in ratio of 1:3;
(E') pasteurizing the foundation solution at 85° C. for 4 minutes, then let it cool, and adjusting the Brix to 6 to obtain a pasteurized solution;
(F') adding ethanol 95% at a ratio of 3% (v/v) to the pasteurized solution, adjusting the pH to 5 by acetic acid 1.5%, then adding *Acetobacter aceti* bacteria in ratio of 1.2% (v/v), and fermenting for 7 days to obtain a solution after fermentation; and
(G') filtering the solution after fermentation to obtain the fruit vinegar.

In view of the foregoing, another objective of the present invention is to the rice alcohol has alcohol range 30%-50% obtained by fermenting a homogeneous mixture twice, then distilling and aging the alcohol using an alcohol aged machine or alcohol aging equipment;
wherein the homogeneous mixture includes 600 parts of a cooked rice mixture, and (1-2) parts of a wine yeast ingredient;
the cooked rice mixture is cooked from 3 parts glutinous rice with 1 part plain rice, 0.2 part shelled green beans, and 4.5 parts water;
wherein the wine yeast ingredient includes 11 parts of a rice flour, (0.6-0.8) parts of an extracted herbal, and (0.001-0.1) parts of a yeast ingredient;
the extracted herbal is extracted from a herbal mixture crushed/chopped, and soaked in solvent, or saturated brine solution; the herbal mixture comprising: *Myristica fragrans* Houtt., *Curcuma aromatica* Salisb., *Atractylodes macrocephala* Koidz., *Mentha arvensis* L., *Amomum aromaticum* Roxb., *Glycyrrhiza uralensis* Fisch., *Foeniculum vulgare* Mill., *Illicium verum* Hook. f., and Cortex *Cinnamomi cassiae*;
the yeast ingredient is selected from the group consisting of *Saccharomyces cerevisiae* NH2, *Saccharomyces cerevisiae* NT3, *Saccharomyces cerevisiae* MS42, *Saccharomyces cerevisiae* CM3.2, *Saccharomyces cerevisiae* D8, *Saccharomyces cerevisiae* NM11, and *Candida tropicalis* NM2.

Finally, the purpose of the invention is to provide the microorganism solution comprising performing in a specific order from (A) to (E):
(A) creating a first suspension solution comprising performing in a specific order from (a1) to (c1):
(a1) activating *Bacillus* sp. TV11 on the Nutrient agar medium, incubating at 37° C. for a period of 36-48 hours to obtain an activated *Bacillus* sp. TV11;
(b1) inoculating a single colony of the activated *Bacillus* sp. TV11 into a test tube containing 10 ml of Nutrient broth medium, shaking at 200 rpm for 24 hours at 37° C. to obtain an increased first biomass solution; and
(c1) inoculating the increased first biomass solution into Nutrient broth medium at a ratio of (1-3): 100, shaking at 200 rpm for 24 hours at 37° C. to obtain the first suspension solution;
(B) creating a second suspension solution comprising performing in a specific order from (a2) to (c2):
(a2) activating *Lactobacillus* sp. T432 on the Man Rogosa Sharpe (MRS) agar medium, incubating at 37° C. for a period of 36-48 hours to obtain an activated *Lactobacillus* sp. T432;
(b2) inoculating a single colony of the activated *Lactobacillus* sp. T432 into a test tube containing 10 ml of MRS broth medium, shaking at 200 rpm for 24 hours at 37° C. to obtain an increased second biomass solution; and (c2) inoculating the increased second biomass solution into MRS broth medium at a ratio of (1-3): 100, shaking at 200 rpm for 24 hours at 37° C. to obtain the second suspension solution;

(C) creating a third suspension solution comprising performing in a specific order from (a3) to (c3):

(a3) activating *Lactobacillus plantarum* VTCC 431 on the MRS agar medium, incubating at 37° C. for a period of 36-48 hours to obtain an activated *Lactobacillus plantarum* VTCC 431;

(b3) inoculating a single colony of the activated *Lactobacillus plantarum* VTCC 431 into a test tube containing 10 ml of MRS broth medium, shaking at 200 rpm for 24 hours at 37° C. to obtain an increased third biomass solution; and (c3) inoculating the increased third biomass solution into MRS broth medium at a ratio of (1-3): 100, shaking at 200 rpm for 24 hours at 37° C. to obtain the third suspension solution;

(D) creating a fourth suspension solution comprising performing in a specific order from (a4) to (c4):

(a4) activating *Lactobacillus bulgaricus* VTCC 703 on the MRS agar medium, incubating at 37° C. for a period of 36-48 hours to obtain an activated *Lactobacillus bulgaricus* VTCC 703;

(b4) inoculating a single colony of the activated *Lactobacillus bulgaricus* VTCC 703 into a test tube containing 10 ml of MRS broth medium, shaking at 200 rpm for 24 hours at 37° C. to obtain an increased fourth biomass solution; and (c4) inoculating the increased fourth biomass solution into MRS broth medium at a ratio of (1-3): 100, shaking at 200 rpm for 24 hours at 37° C. to obtain the fourth suspension solution;

(E) mixing (1-2) parts of the first suspension solution with (1-2) parts of the second suspension solution, (1-2) parts of the third suspension solution, and (1-2) parts of the fourth suspension solution to obtain the microorganism solution.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWING

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the appended claims.

Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

It should also be noted that the term "dissolve/dissolving/dissolved" is used in the invention understood to mean the uniform distribution, or complete dissolution of, substances present in a solution/mixture.

Figure 1:
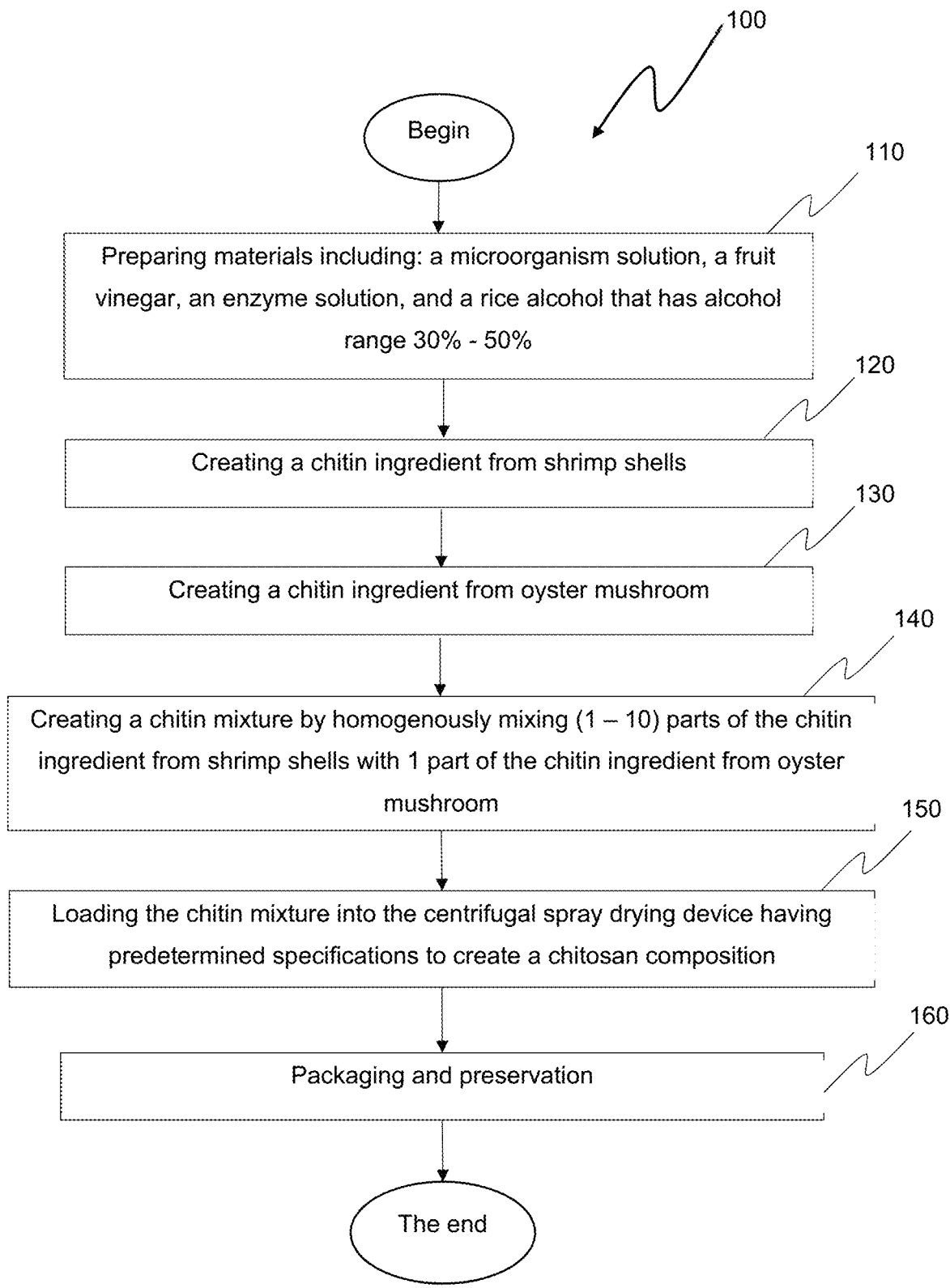
FIG. 1 is a flowchart illustrating a method of manufacturing the chitosan composition according to an embodiment of the present invention.

One embodiment of the invention is now described with reference to FIG. 1. FIG. 1 illustrating a specific process of manufacturing the chitosan composition 100 ("method 100") based on the above principle in accordance with an exemplary embodiment of the present invention. In particular, method 100 includes the following steps:

At step 110, prepare materials including: a microorganism solution, a fruit vinegar, an enzyme solution, and a rice alcohol that has alcohol range 30%-50%.

According to the embodiment of the invention, the microorganism solution obtained from a process 200 will be described in detail later below. The fruit vinegar obtained from a process 300 will be described in detail later below.

According to the embodiment of the invention, prepare the enzyme solution by performing steps from (A") to (B") including:

(A") creating an enzyme preparation by homogeneously mixing (1-3) parts of a protease ingredient with 1 part of a lipase ingredient; and (B") creating the enzyme solution by homogeneously mixing (3-5) parts of the enzyme preparation with (5000-10000) parts of the water.

According to the embodiment of the invention, prepare the rice alcohol has alcohol range 30%-50% by fermenting a homogeneous mixture twice, then distilling and aging the alcohol using an alcohol aged machine or alcohol aging equipment.

According to the preferred embodiment of the present invention, the rice alcohol has alcohol range 45%-50%.

According to the embodiment of the invention, the homogeneous mixture includes 600 parts of a cooked rice mixture, and (1-2) parts of a wine yeast ingredient.

According to the preferred embodiment of the invention, the cooked rice mixture is cooked from 3 parts glutinous rice with 1 part plain rice, 0.2 part shelled green beans, and 4.5 parts water.

According to the embodiment of the invention, the wine yeast ingredient includes 11 parts of a rice flour, (0.6-0.8) parts of an extracted herbal, and (0.001-0.1) parts of a yeast ingredient.

According to the embodiment of the invention, the wine yeast ingredient includes 11 parts of the rice flour, (0.6-0.8) parts of the extracted herbal, and (0.01-0.1) parts of the yeast ingredient.

According to the preferred embodiment of the invention, the wine yeast ingredient includes 11 parts of the rice flour, 0.7 parts of the extracted herbal, and (0.01-0.1) parts of the yeast ingredient.

According to the embodiment of the invention, the extracted herbal is extracted from a herbal mixture crushed/chopped, and soaked in solvent, or saturated brine solution. The herbal mixture is listed in Table 2 below, including: *Myristica fragrans* Houtt., *Curcuma aromatica* Salisb., *Atractylodes macrocephala* Koidz., *Mentha arvensis* L., *Amomum aromaticum* Roxb., *Glycyrrhiza uralensis* Fisch., *Foeniculum vulgare* Mill., *Illicium verum* Hook. f., and Cortex *Cinnamomi cassiae*.

TABLE 2

Components of the herbal mixture are used in the embodiment of the present invention

| No. | Species | Collection region | Used parts |
|---|---|---|---|
| 1 | *Myristica fragrans* Houtt. | Vietnam | seeds |
| 2 | *Curcuma aromatica* Salisb. | | rhizomes |
| 3 | *Atractylodes macrocephala* Koidz. | | rhizomes |
| 4 | *Mentha arvensis* L. | | leaves |
| 5 | *Amomum aromaticum* Roxb. | | fruits |
| 6 | *Glycyrrhiza uralensis* Fisch. | | rhizomes |
| 7 | *Foeniculum vulgare* Mill. | | fruits |
| 8 | *Illicium verum* Hook. f. | | fruits |
| 9 | Cortex *Cinnamomi cassiae* | | bark |

According to the embodiment of the invention, the yeast ingredient is selected from the group consisting of *Saccharomyces cerevisiae* NH2, *Saccharomyces cerevisiae* NT3, *Saccharomyces cerevisiae* MS42, *Saccharomyces cerevisiae* CM3.2, *Saccharomyces cerevisiae* D8, *Saccharomyces cerevisiae* NM11, and *Candida tropicalis* NM2; all are listed in Table 3 below.

TABLE 3

The strains of yeasts present in the yeast ingredient according to the embodiment of the invention

| No. | Type species | Storage location | Reference |
|---|---|---|---|
| 1 | *Saccharomyces cerevisiae* NH2 | Institute of Biotechnology Research and Development, Can Tho University | Bình, L. N., Thành, N. V., Thảo, H. P., & Khánh, T. V. (2015). Isolating and screening strongly active yeast strains from local alcoholic fermentation starters. CTU Journal of Science and Technology, (39), 18-28. |
| 2 | *Saccharomyces cerevisiae* NT3 | | |
| 3 | *Saccharomyces cerevisiae* MS42 | Institute of Biotechnology and Food Industry, Hanoi University of Science and Technology | Nguyễn Văn Quyên et al (2018). The influence of some factors on the production of alcohol whisky by *Saccharomyces cerevisiae* MS42 from barley malt. Journal of Biotechnology 16(3), 525-532. |
| 4 | *Saccharomyces cerevisiae* CM3.2 | Institute of Biotechnology Research and Development, Can Tho University | Đoàn Thị Kiều Tiên el al (2018). Evaluation of total polyphenol and antioxidant capacity in wine fermentation of three-leaf cayratia from Ca Mau province using *Saccharomyces cerevisiae* CM3.2. CTU Journal of Science and Technology, 55 (2), 285-291. |
| 5 | *Saccharomyces cerevisiae* D8 | Institute of Biotechnology Research and Development, Tan Trao University | Le Thuong, H. T., Thuy, T. T., & Hao, N. Q. (2018). Improvement of the ethanol production of *saccharomyces cerevisiae* D8 by the random mutagenesis. Vietnam Journal of Biotechnology, 16(2), 337-344. |
| 6 | *Saccharomyces cerevisiae* NM11 | Institute of Biotechnology Research and Development, Hue University | Đỗ Thị Bích Thủy et al (2023). Effect of some factors on the content of the Compounds in watermelon juice fermented by *Saccharomyces cerevisiae* NM11. Journal of Agricultural Science and Technology. |
| 7 | *Candida tropicalis* NM2 | Institute of Biotechnology Research and Development, Hanoi National University of Education | Doan Van Thuoc et al (2015). Characterization of alcohol producing yeast isolated from fermented fruit juice of *sonneratia caseolaris*. Vietnam Journal of Biotechnology, 37(1), 69-75. |

The term "homogeneous/homogeneously" is understood to mean the uniform distribution, or complete dissolution of, substances present in a solution/mixture.

At step 120, creating a chitin ingredient from shrimp shells comprising performing in a specific order from (a) to (c):
- (a) collecting a molting shell of shrimp, then washing to remove impurities, and soaking with HCl solution in a ratio of 1: (3-5) (w/v) for 15-20 days, then filtering to remove liquid, washing twice with the rice alcohol has alcohol range 30%-50 to obtain a first temporary mixture; in which HCl solution obtained by diluting a solution concentrated HCl contains 40% (concentrated grade) with water to 5%-18% HCl solution;
- (b) treating the first temporary mixture to obtain a basic solution including:
    dissolving a quicklime (CaO) ingredient in solution concentrated HCl contains 40% (concentrated grade) with combined stirring at 50 rpm for 5 minutes to obtain a solution 1;
    admixing the first temporary mixture to the solution 1 with combined stirring at 50 rpm for 5 minutes, then stop stirring and let stand for 7-10 days at 28° C.-40° C. to obtain the basic solution;
    wherein a ratio of the first temporary mixture and the quicklime (CaO) ingredient is 1: (2-5) (w/w);
    wherein a ratio of the quicklime (CaO) ingredient and solution concentrated HCl contains 40% (concentrated grade) is 1: (2-5) (w/v);
- (c) admixing 1 part of the enzyme solution at step 110 into 10 parts of the basic solution, then stop stirring and let stand for 12-18 hours to obtain the chitin ingredient from shrimp shells.

According to the priority embodiment of the invention, at step (b) the ratio of the first temporary mixture and the quicklime (CaO) ingredient is 1:3 (w/w).

According to the embodiment of the invention, the molting shell of shrimp is selected from the group consisting of litopenaeus vannamei (*Penaeus vannamei*), *Penaeus monodon, Penaeus merguiensis, Macrobrachium rosenbergii, Metapenaeus ensis, Macrobrachium lanchesteri, Fenneropenaeus merguiensis, Penaeus semisulcatus*, and a combination thereof; all are listed in Table 4 below.

TABLE 4

Ingredients of shrimp species present in the shrimp shells according to the embodiment of the invention

| No. | Species | Collection region | Time to raise fully mature shrimp |
|---|---|---|---|
| 1 | litopenaeus vannamei (*Penaeus vannamei*) | Mekong Delta region: Soc Trang, Bac Lieu, Ca Mau, Kien Giang, Tra Vinh provinces; Central region: Binh Dinh, Phu Yen, Khanh Hoa, Ninh Thuan, Binh Thuan provinces; Southeast region: Ba Ria-Vung Tau, Tien Giang, Long An provinces; Northern region: Quang Ninh, Thai Binh, Nam Dinh provinces. | 180 days |
| 2 | Penaeus monodon | Mekong Delta region: Ca Mau, Bac Lieu, Kien Giang, Tra Vinh, Soc Trang, An Giang, Tien Giang provinces; Central Coast region: Binh Dinh, Phu Yen, Ninh Thuan, Binh Thuan provinces; North Central region: Thanh Hoa, Nghe An, Ha Tinh provinces; Southeast region: Ba Ria-Vung Tau, Dong Nai provinces; Northern region: Thai Binh, Nam Dinh, Quang Ninh provinces. | 4 months |
| 3 | Penaeus Merguiensis | Mekong Delta region: Ca Mau, Bac Lieu, Tra Vinh, Soc Trang, An Giang, Kien Giang provinces; Central Coast region: Binh Dinh, Phu Yen, Khanh Hoa, Ninh Thuan, Binh Thuan provinces; Southeast region: Ba Ria-Vung Tau, Tien Giang, Long An provinces. | 3-4 months |
| 4 | Macrobrachium rosenbergii | Ca Mau, Kien Giang, Can Tho, Long An, Dong Nai, Ben Tre, Soc Trang, An Giang provinces. | 100-135 days |
| 5 | Metapenaeus ensis | Mekong Delta region: Ca Mau, Bac Lieu, Tra Vinh, Soc Trang, An Giang, Kien Giang provinces; Central Coast region: Binh Dinh, Phu Yen, Khanh Hoa, Ninh Thuan, Binh Thuan provinces; Southeast region: Ba Ria-Vung Tau, Tien Giang, Long An provinces. | 3-4 months |
| 6 | Macrobrachium lanchesteri | North: Red River Basin (Hanoi, Hai Phong, Hai Duong provinces); Thai Binh river basin (Thai Binh, Nam Dinh provinces); Cau River basin (Bac Giang, Bac Ninh provinces); | 3-4 months |

TABLE 4-continued

Ingredients of shrimp species present in the shrimp shells according to the embodiment of the invention

| No. | Species | Collection region | Time to raise fully mature shrimp |
|---|---|---|---|
| | | Central region:<br>Ma River basin (Thanh Hoa province);<br>Gianh river basin (Quang Binh province);<br>Vu Gia-Thu Bon river basin (Quang Nam, Da Nang province);<br>Southern:<br>Dong Nai River Basin (Dong Nai province, Ho Chi Minh City);<br>Tien and Hau river basins (Mekong Delta);<br>Coastal lagoon area (Ca Mau, Kien Giang province). | |
| 7 | Fenneropenaeus Merguiensis | Mekong Delta region: Ca Mau, Bac Lieu, Tra Vinh, Soc Trang, An Giang, Kien Giang provinces;<br>Central Coast region: Binh Dinh, Phu Yen, Khanh Hoa, Ninh Thuan, Binh Thuan provinces;<br>Southeast region: Ba Ria-Vung Tau, Tien Giang, Long An provinces. | 3-4 months |
| 8 | Penaeus Semisulcatus | Mekong Delta region: Ca Mau, Bac Lieu, Tra Vinh, Soc Trang, An Giang, Kien Giang provinces;<br>Central Coast region: Binh Dinh, Phu Yen, Khanh Hoa, Ninh Thuan, Binh Thuan provinces;<br>Southeast region: Ba Ria-Vung Tau, Tien Giang, Long An provinces. | 3-4 months |

According to the embodiment of the invention, the molting shell of shrimp is a molting shell of shrimp from 60-180 days old shrimp.

According to the embodiment of the invention, the molting shell of shrimp is a molting shell of shrimp from 61-90 days old shrimp.

According to the embodiment of the invention, the molting shell of shrimp is a molting shell of shrimp from 71-80 days old shrimp.

Refer to the survey results of chitin, mineral and protein content analyzed from molting shrimp shells at different age stages (O1-O6), all listed in Table 5 below.

TABLE 5

Comparison of chitin, mineral and protein content analyzed from molting shrimp shells at different age stages (O1-O6) according to the invention's embodiment

| Species | Stages | Age (days) | Minerals (%) | Protein (%) | Chitin (%) |
|---|---|---|---|---|---|
| litopenaeus vannamei | O1 | 31-60 | 54.95 ± 2.6 | 12.45 ± 1.1 | 20.1 ± 0.8 |
| (Penaeus vannamei) | O2 | 61-70 | 60.8 ± 1.9 | 10.4 ± 0.7 | 23.4 ± 0.5 |
| | O3 | 71-80 | 53.5 ± 0.5 | 12.6 ± 0.6 | 23.7 ± 0.2 |
| | O4 | 81-90 | 55.1 ± 0.8 | 12.5 ± 0.8 | 23.5 ± 0.7 |
| | O5 | >90 | 55.8 ± 1.9 | 12.7 ± 0.7 | 23.6 ± 0.5 |
| Penaeus monodon | O1 | 31-60 | 53.66 ± 2.2 | 11.75 ± 1.3 | 19.5 ± 0.6 |
| | O2 | 61-70 | 62.8 ± 1.4 | 9.84 ± 0.5 | 22.7 ± 0.8 |
| | O3 | 71-80 | 52.2 ± 0.7 | 11.6 ± 0.6 | 22.5 ± 0.3 |
| | O4 | 81-90 | 54.5 ± 0.6 | 11.8 ± 0.4 | 22.1 ± 0.2 |
| | O5 | >90 | 54.7 ± 1.3 | 11.95 ± 0.7 | 22.3 ± 0.6 |
| Penaeus Merguiensis | O1 | 31-60 | 55.45 ± 1.7 | 12.55 ± 1.2 | 20.8 ± 0.5 |
| | O2 | 61-70 | 61.9 ± 1.1 | 10.3 ± 0.9 | 24.1 ± 0.3 |
| | O3 | 71-80 | 52.7 ± 0.6 | 13.2 ± 0.4 | 24.9 ± 0.2 |
| | O4 | 81-90 | 56.2 ± 0.1 | 13.4 ± 0.5 | 24.6 ± 0.3 |
| | O5 | >90 | 56.5 ± 1.5 | 13.6 ± 0.2 | 24.5 ± 0.7 |
| Macrobrachium | O1 | 31-60 | 54.12 ± 1.9 | 11.97 ± 1.5 | 20.5 ± 0.2 |
| rosenbergii | O2 | 61-70 | 63.4 ± 1.8 | 9.76 ± 0.8 | 23.5 ± 0.4 |
| | O3 | 71-80 | 53.5 ± 0.6 | 11.8 ± 0.5 | 23.8 ± 0.7 |
| | O4 | 81-90 | 54.8 ± 0.7 | 11.7 ± 0.8 | 23.4 ± 0.4 |
| | O5 | >90 | 54.9 ± 1.1 | 11.9 ± 0.3 | 23.3 ± 0.8 |
| Metapenaeus ensis | O1 | 31-60 | 56.1 ± 1.2 | 13.11 ± 1.3 | 21.6 ± 0.7 |
| | O2 | 61-70 | 61.3 ± 1.4 | 11.3 ± 0.4 | 23.1 ± 0.4 |
| | O3 | 71-80 | 53.9 ± 0.5 | 13.8 ± 0.7 | 23.7 ± 0.9 |
| | O4 | 81-90 | 55.7 ± 0.7 | 13.5 ± 0.3 | 23.4 ± 0.7 |
| | O5 | >90 | 55.9 ± 1.4 | 13.7 ± 0.6 | 23.3 ± 0.3 |

TABLE 5-continued

Comparison of chitin, mineral and protein content analyzed from molting shrimp shells at different age stages (O1-O6) according to the invention's embodiment

| Species | Stages | Age (days) | Minerals (%) | Protein (%) | Chitin (%) |
|---|---|---|---|---|---|
| Macrobrachium | O1 | 31-60 | 55.84 ± 1.6 | 12.45 ± 1.6 | 21.2 ± 0.7 |
| lanchesteri | O2 | 61-70 | 64.5 ± 1.2 | 10.63 ± 0.7 | 24.2 ± 0.3 |
| | O3 | 71-80 | 54.1 ± 0.4 | 12.6 ± 0.8 | 24.9 ± 0.4 |
| | O4 | 81-90 | 55.2 ± 0.5 | 12.4 ± 0.6 | 24.6 ± 0.7 |
| | O5 | >90 | 54.4 ± 1.3 | 12.7 ± 0.5 | 24.7 ± 0.5 |
| Fenneropenaeus | O1 | 31-60 | 54.77 ± 2.0 | 12.25 ± 1.3 | 20.3 ± 0.7 |
| Merguiensis | O2 | 61-70 | 60.5 ± 1.5 | 10.1 ± 0.5 | 23.2 ± 0.7 |
| | O3 | 71-80 | 53.8 ± 0.4 | 12.9 ± 0.3 | 23.8 ± 0.6 |
| | O4 | 81-90 | 55.3 ± 0.9 | 12.4 ± 0.6 | 23.4 ± 0.6 |
| | O5 | >90 | 55.7 ± 1.7 | 12.6 ± 0.8 | 23.5 ± 0.4 |
| Penaeus Semisulcatus | O1 | 31-60 | 55.5 ± 1.8 | 12.65 ± 1.6 | 20.8 ± 0.5 |
| | O2 | 61-70 | 61.7 ± 1.1 | 10.5 ± 0.6 | 22.6 ± 0.2 |
| | O3 | 71-80 | 54.4 ± 0.3 | 12.7 ± 0.8 | 22.9 ± 0.8 |
| | O4 | 81-90 | 56.2 ± 0.8 | 12.2 ± 0.5 | 22.5 ± 0.6 |
| | O5 | >90 | 56.5 ± 1.4 | 12.4 ± 0.7 | 22.7 ± 0.4 |

At step 130, creating a chitin ingredient from oyster mushroom comprising performing in a specific order from (a') to (d'):
- (a') collecting oyster mushrooms, then washing to remove impurities, and soaking with the fruit vinegar at step 110 in a ratio of 1: (3-5) (w/v) for 15-20 days, then filtering to remove liquid, and washing twice with the rice alcohol has alcohol range 30%-50% to obtain a second temporary mixture; wherein the fruit vinegar has a concentration of 35%-55%;
- (b') treating the second temporary mixture to obtain a basic temporary solution including:
  dissolving the quicklime (CaO) ingredient in solution concentrated HCl contains 40% (concentrated grade) with combined stirring at 50 rpm for 5 minutes to obtain the solution 1;
  admixing the second temporary mixture to the solution 1 with combined stirring at 50 rpm for 5 minutes, then stop stirring and let stand for 7-10 days at 28° C.-40° C. to obtain the basic temporary solution; wherein a ratio of the second temporary mixture and the quicklime (CaO) ingredient is 1: (3-5) (w/w); wherein a ratio of the quicklime (CaO) ingredient and solution concentrated HCl contains 40% (concentrated grade) is 1: (2-5) (w/v);
- (c') admixing the microorganism solution at step 110 into the basic temporary solution at a ratio of (1-2): 10 (w/v) to obtain a foundation temporary solution; and
- (d') adjusting pH of the foundation temporary solution reached 6.8-7.2, then fermenting at 30° C.-40° C. for 125-135 hours to obtain the chitin temporary mixture from oyster mushroom.

According to the priority embodiment of the invention, at step (b') the ratio of the second temporary mixture and the quicklime (CaO) ingredient is 1:4 (w/w).

According to another embodiment of the invention, replacing the quicklime (CaO) ingredient with a solution lime for betel chewing. The solution lime for betel chewing is obtained by dissolving 1 part of a powdered lime for betel chewing with 0.5-5 parts of the water; wherein the powdered lime for betel chewing is obtained by calcining (burning) shells, coral, or limestone. The powdered lime for betel chewing comprising chemical components: calcium hydroxide $Ca(OH)_2$, and calcium carbonate $CaCO_3$.

According to the embodiment of the invention, oyster mushrooms listed in Table 6 below, including: Pleurotus pulmonarius, Pleurotus cf. floridanus, Pleurotus ostreatus, Pleurotus citrinopileutus, and a combination thereof.

TABLE 6

Ingredients of species present in the oyster mushrooms according to the embodiment of the invention

| No. | Species | References |
|---|---|---|
| 1 | Pleurotus pulmonarius | Pham Van Loc et al (2023). Identification of Oyster Mushroom (Pleurotus spp.) Strains in the South Vietnam based on Morphological Characteristics and ITS Sequencing. Vietnam J. Agri. Sci, 21(12): 1569-1580 |
| 2 | Pleurotus cf. floridanus | |
| 3 | Pleurotus ostreatus | |
| 4 | Pleurotus citrinopileatus | Nguyen Thi Thom et al (2018). Study of cultivating golden oyster mushroom Pleurotus citrinopileatus utilization of agricultural waste. Journal of Science. University of Education, Hue University, 01(45): 138-148 |

At step 140, creating a chitin mixture by homogenously mixing the chitin ingredient from shrimp shells at step 120 with the chitin ingredient from oyster mushroom at step 130; wherein the ratio of the chitin ingredient from shrimp shells and the chitin ingredient from oyster mushroom is (1-10): 1 (w/w).

According to the embodiment of the invention, the ratio of the chitin ingredient from shrimp shells and the chitin ingredient from oyster mushroom is (1-7): 1 (w/w).

According to the embodiment of the invention, the ratio of the chitin ingredient from shrimp shells and the chitin ingredient from oyster mushroom is (1-5): 1 (w/w).

According to the embodiment of the invention, the ratio of the chitin ingredient from shrimp shells and the chitin ingredient from oyster mushroom is (1-3): 1 (w/w).

At step 150, loading the chitin mixture into a centrifugal spray drying device having predetermined specifications to create the chitosan composition; in which predetermined specifications include: a rotate speed of 1200 rpm for 3-5 hours at temperature 20° C.-28° C. Step 150 can be done with the centrifugal spray drying device and other similar devices. The centrifugal spray drying device has been known in previous art so the description of the structure and its operating principle will not be described in detail in the invention.

According to the embodiment of the invention, at step 150, the chitosan composition has a pH of 7-8.5.

According to the embodiment of the invention, at step 150, the chitosan composition has a pH of 8-8.5.

According to the embodiment of the invention, at step 150, time is 4-5 hours.

According to the embodiment of the invention, at step 150, time is 5 hours.

According to the embodiment of the invention, at step 150, temperature is 23° C.-26° C.

According to the embodiment of the invention, at step 150, temperature is 25° C.

Finally, at step 160, packaging the chitosan composition at step 150 and preservation.

According to other embodiments of the invention, the method 100 further comprising step drying the chitosan composition at 70° C. for 5-10 minutes before the step 160 packaging and preservation.

According to the invention, the chitosan composition obtained by method 100 is edible and soluble in saliva secreted in the oral cavity by more than 95%, preferably more than 97%, preferably more than 98%.

It should be noted that the term "admixed/mixed/admixing/mixing" as used in the present invention is understood to mean adding, or reacting, or dissolving homogeneously, or evenly, components in the same solution/mixture.

Figure 2:
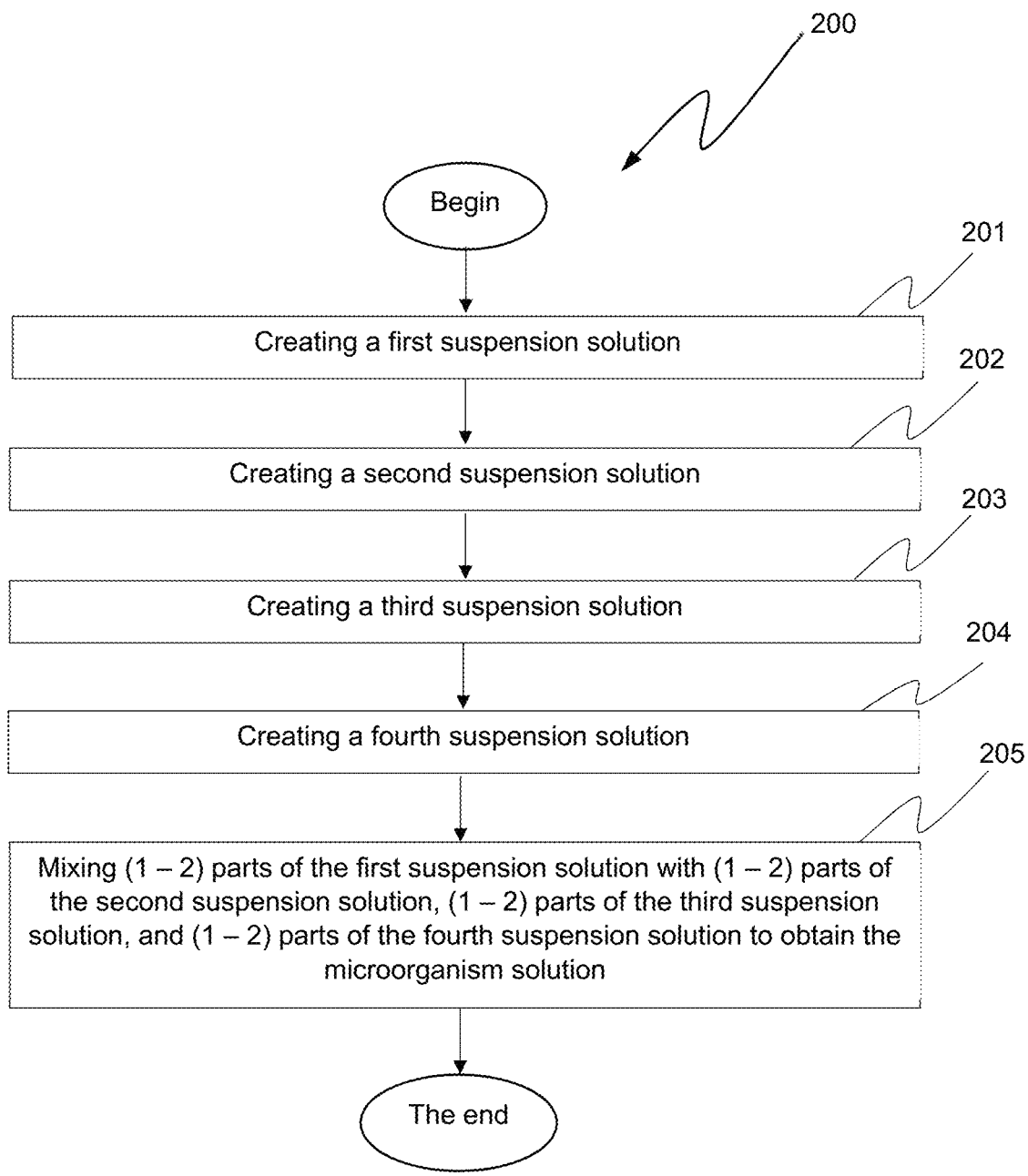
FIG. 2 is a flowchart illustrating a process for preparing the microorganism solution according to an embodiment of the present invention.

Now referring to FIG. 2, the process for preparing the microorganism solution 200 ("process 200") based on the above principle in accordance with an exemplary embodiment of the present invention. In particular, process 200 includes the following steps:

At step 201, creating a first suspension solution comprising performing in a specific order from (a1) to (c1):
- (a1) activating *Bacillus* sp. TV11 on the Nutrient agar medium, incubating at 37° C. for a period of 36-48 hours to obtain an activated *Bacillus* sp. TV11;
- (b1) inoculating a single colony of the activated *Bacillus* sp. TV11 into a test tube containing 10 ml of Nutrient broth medium, shaking at 200 rpm for 24 hours at 37° C. to obtain an increased first biomass solution; and
- (c1) inoculating the increased first biomass solution into Nutrient broth medium at a ratio of (1-3): 100, shaking at 200 rpm for 24 hours at 37° C. to obtain the first suspension solution.

At step 202, creating a second suspension solution comprising performing in a specific order from (a2) to (c2):
- (a2) activating *Lactobacillus* sp. T432 on the Man Rogosa Sharpe (MRS) agar medium, incubating at 37° C. for a period of 36-48 hours to obtain an activated *Lactobacillus* sp. T432;
- (b2) inoculating a single colony of the activated *Lactobacillus* sp. T432 into a test tube containing 10 ml of MRS broth medium, shaking at 200 rpm for 24 hours at 37° C. to obtain an increased second biomass solution; and
- (c2) inoculating the increased second biomass solution into MRS broth medium at a ratio of (1-3): 100, shaking at 200 rpm for 24 hours at 37° C. to obtain the second suspension solution.

At step 203, creating a third suspension solution comprising performing in a specific order from (a3) to (c3):
- (a3) activating *Lactobacillus plantarum* VTCC 431 on the MRS agar medium, incubating at 37° C. for a period of 36-48 hours to obtain an activated *Lactobacillus plantarum* VTCC 431;
- (b3) inoculating a single colony of the activated *Lactobacillus plantarum* VTCC 431 into a test tube containing 10 ml of MRS broth medium, shaking at 200 rpm for 24 hours at 37° C. to obtain an increased third biomass solution; and
- (c3) inoculating the increased third biomass solution into MRS broth medium at a ratio of (1-3): 100, shaking at 200 rpm for 24 hours at 37° C. to obtain the third suspension solution.

At step 204, creating a fourth suspension solution comprising performing in a specific order from (a4) to (c4):
- (a3) activating *Lactobacillus plantarum* VTCC 431 on the MRS agar medium, incubating at 37° C. for a period of 36-48 hours to obtain an activated *Lactobacillus plantarum* VTCC 431;
- (b3) inoculating a single colony of the activated *Lactobacillus plantarum* VTCC 431 into a test tube containing 10 ml of MRS broth medium, shaking at 200 rpm for 24 hours at 37° C. to obtain an increased third biomass solution; and
- (c3) inoculating the increased third biomass solution into MRS broth medium at a ratio of (1-3): 100, shaking at 200 rpm for 24 hours at 37° C. to obtain the third suspension solution.

Finally, at step 205, mixing (1-2) parts of the first suspension solution at step 201 with (1-2) parts of the second suspension solution at step 202, (1-2) parts of the third suspension solution at step 203, and (1-2) parts of the fourth suspension solution at step 204 to obtain the microorganism solution.

According to the embodiment of the present invention, the microorganism solution contains strains of microorganisms including *Bacillus* sp. TV11, *Lactobacillus* sp. T432, *Lactobacillus plantarum* VTCC 431, and *Lactobacillus bulgaricus* VTCC 703, all listed in Table 7 below.

TABLE 7

The strains of microorganisms present in the microorganism solution according to the embodiment of the invention

| Genus | Type species | Storage location | Reference |
| --- | --- | --- | --- |
| *Bacillus* | *Bacillus* sp. TV11 | Institute of Biotechnology Research and Development, Can Tho University | Phong, H. X., Linh, L. Đ., Nam, P. H., Thanh, N. N., & Long, B. H. Đ. (2020). Production of chitin from shrimp shells (*Penaeus monodon*) using *Bacillus* sp. TV11 and *Lactobacillus* sp. T342. TNU Journal of Science and Technology, 225(08), 230-238. |
| *Lactobacillus* | *Lactobacillus* sp. T432 | | |

TABLE 7-continued

The strains of microorganisms present in the microorganism solution according to the embodiment of the invention

| Genus | Type species | Storage location | Reference |
|---|---|---|---|
| | Lactobacillus plantarum VTCC 431 Lactobacillus bulgaricus VTCC 703 | Vietnam Type Culture Collection-Vietnam National University, Hanoi | Boi, V. N., Trang, N. T. M., Thao, N., T., P., Chung, L., P., Yen, H., T., B. (2016). Study on using lactic acid bacteria for demineralization and deproteinization of heads and shells of shrimp in chitosan production. Journal of Fisheries Science and Technology (01), 11-19. |

Figure 3:
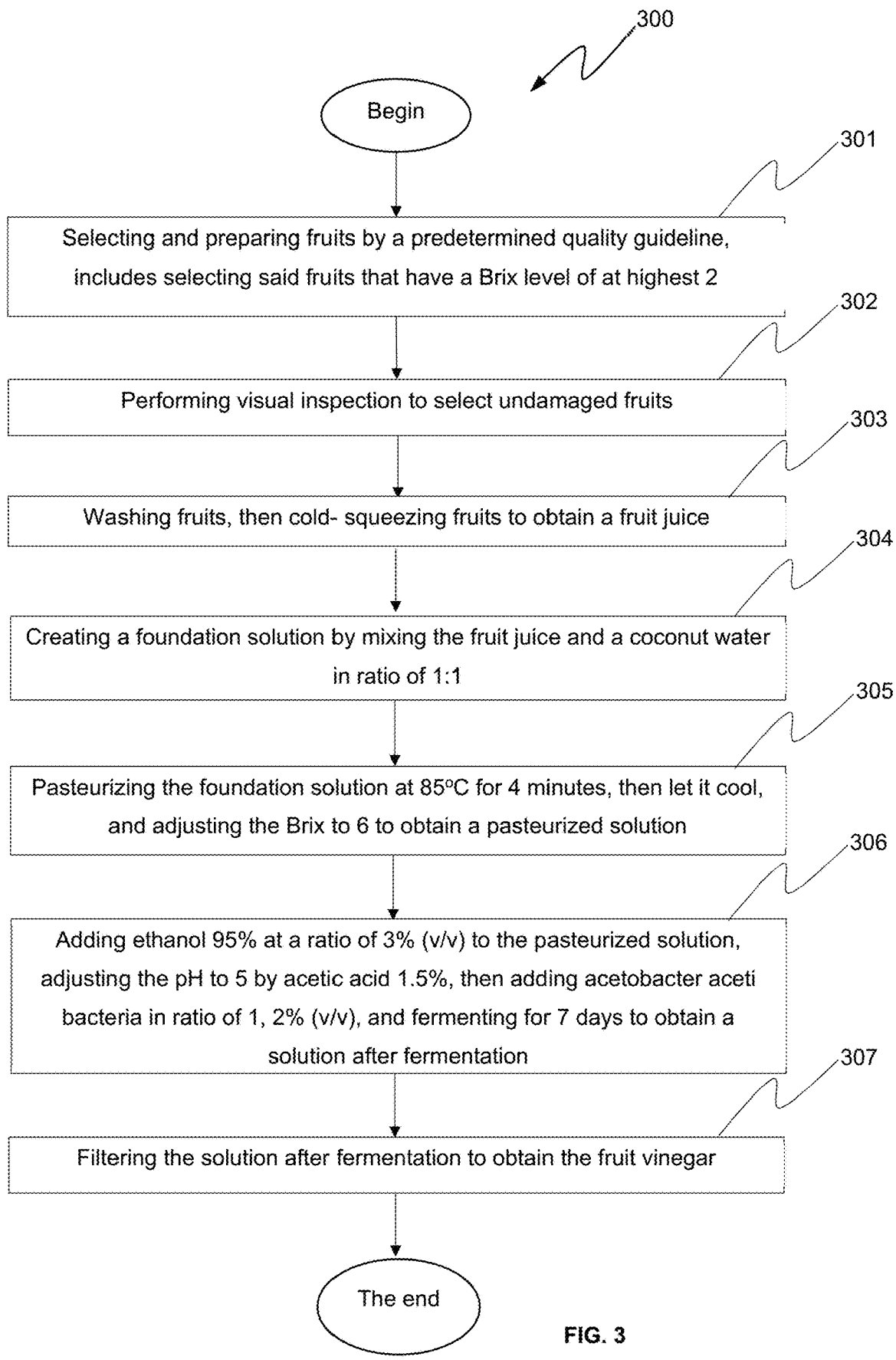
FIG. 3 is a flowchart illustrating a process for preparing the fruit vinegar according to an embodiment of the present invention.

Referring to FIG. 3, the process for preparing the fruit vinegar 300 ("process 300") based on the above principle in accordance with an exemplary embodiment of the present invention. In particular, process 300 includes the following steps:

At step 301, selecting and preparing fruits by a predetermined quality guideline, includes selecting said fruits that have a Brix level of at highest 2.

According to the embodiment of the invention, said fruits is selected from the group consisting of ambarella (*Spondias dulcis*), plum (*Prunus salicina*), apricot (*Prunus armeniaca* (L.)), crocodile fruit (*Dracontomelon duperreanum*), star gooseberry (*Phyllanthus acidus* (L.)), and a combination thereof, all listed in Table 8 below.

TABLE 8

The fruits ingredients for creating the fruit vinegar according to the embodiment of the present invention

| Fruits | Scientific name | Collection region | Used part |
|---|---|---|---|
| Ambarella | *Spondias dulcis* | Central Vietnam | Fruit |
| Plum | *Prunus salicina* | Southern Vietnam | |
| Apricot | *Prunus armeniaca* (L.) | Northern Vietnam | |
| Crocodile fruit/ Dracontomelon | *Dracontomelon duperreanum* | Northern Vietnam | |
| Star gooseberry | *Phyllanthus acidus* (L.) | Northern Vietnam | |

At step 302, performing visual inspection to select undamaged fruits.

At step 303, washing fruits and cold-squeezing fruits to obtain a fruit juice.

At step 304, creating a foundation solution by mixing the fruit juice at step 303 and the coconut water in a ratio of 1:1.

At step 305, pasteurizing the foundation solution at step 304 at 85° C. for 4 minutes, then let it cool, and adjusting the Brix to 6 to obtain a pasteurized solution.

At step 306, adding ethanol 95% at a ratio of 3% (v/v) to the pasteurized solution at step 305, adjusting the pH to 5 by acetic acid 1.5%, then adding *Acetobacter aceti* bacteria in ratio of 1, 2% (v/v), and fermenting for 7 days to obtain a solution after fermentation.

Finally, at step 307, filtering the solution after fermentation at step 306 to obtain the fruit vinegar.

In the present invention and the specification of the present application, it should also be noted that the steps washing by distilled water according to method 100, or according to process 200, or according to process 300, all characterized in that the washing temperature of the distilled water is 55° C.-60° C. According to the preferred embodiment of the present invention, washing temperature of the distilled water is 60° C.

According to another embodiment of the invention, the chitosan composition created by method 100 is mixed with a turkey tail mushroom extract ingredient to obtain a complex composition of turkey tail mushroom extract-chitosan.

According to another embodiment of the invention, the chitosan composition created by method 100 is mixed with a turkey tail mushroom extract ingredient, a carboxymethyl cellulose solution 0.375%, a alginate solution 0.375%, a potassium citrate solution, a $AgNO_3$ solution 0.37%, a $Cu(NO_3)_2$ solution 0.723%, a $Zn(NO_3)_2$ solution 3.085%, $Co(NO_3)_2$ solution 0.746%, a $Fe(NO_3)_3$ solution 2.5%, a glycerin ingredient, a vitamin E, a tartrazine ingredient 1%, a $K_2HPO_4$ solution 15%, a mixture extracts/essential oils, and an other ingredient to obtain a composition for prevention and treatment of Early Mortality Syndrome (EMS) shrimp.

The purpose of the following example is to prove that the technical solution in this invention has been successfully researched and tested by the author. Specifically, according to the method 100 applied to create the chitosan composition including the following specific steps:

(Step 1) creating the chitin ingredient from shrimp shells is similar to step 120, characteristic in that:
  at step (a), the soaking ratio between the molting shell of shrimp and HCl solution is 1:5 for 20 days;
  at step (b):
    the ratio of the quicklime (CaO) ingredient and the solution concentrated HCl contains 40% (concentrated grade) is 1:2 (w/v);
    the soaking ratio between the first temporary mixture and the quicklime (CaO) ingredient is 1:3 (w/v); and
  at step (c), time for let stand is 15 hours; and (Step 2) creating the chitin ingredient from oyster mushroom is similar to step 130, characteristic in that:
  at step (a'), the soaking ratio between oyster mushroom and the fruit vinegar is 1:5 for 15 days;
  at step (b'):
    the ratio of the quicklime (CaO) ingredient and the solution concentrated HCl contains 40% (concentrated grade) is 1:2 (w/v);
    the soaking ratio between the second temporary mixture and the quicklime (CaO) ingredient is 1:4 (w/v); and
  at step (c'), the mixing ratio between the microorganism solution and the second temporary mushroom powder is 1.5:10 (w/v); and
  at step (d'), fermenting time is 130 hours;

(Step 3) creating the chitin mixture by homogenously mixing the chitin ingredient from shrimp shells with the chitin ingredient from oyster mushroom is similar to step 140, including five formulas listed in Table 9 below;

(Step 4) creating the chitosan composition is similar to step 150, characteristic in that predetermined specifications including: a rotate speed of 1200 rpm for 5 hours at temperature 25° C.

TABLE 9

Ratio of mixing ingredients for creating the chitin mixture in five formulas according to method 100 of the present invention

| | Ratio (w/w) | |
| --- | --- | --- |
| Formula | The chitin ingredient from shrimp shells | The chitin ingredient from oyster mushroom |
| 1 | 1 | 1 |
| 2 | 3 | 1 |
| 3 | 5 | 1 |
| 4 | 7 | 1 |
| 5 | 10 | 1 |

The present invention is further described in detail with reference to the following the ratio (w/w or v/v) of mixing ingredients to create the microorganism solution according to process 200 including fifteen formulas listed in Table 10 below.

TABLE 10

Ratio of mixing ingredients for creating the microorganism solution in fifteen formulas according to process 200 of the present invention

| | Ratio (w/w or v/v) | | | |
| --- | --- | --- | --- | --- |
| Formula | The first suspension solution | The second suspension solution | The third suspension solution | The fourth suspension solution |
| 1 | 1 | 1 | 1 | 1 |
| 2 | 1 | 1 | 1 | 2 |
| 3 | 1 | 1 | 2 | 1 |
| 4 | 1 | 2 | 1 | 1 |
| 5 | 2 | 1 | 1 | 1 |
| 6 | 2 | 1 | 1 | 2 |
| 7 | 2 | 1 | 2 | 1 |
| 8 | 2 | 2 | 1 | 1 |
| 9 | 1 | 1 | 2 | 2 |
| 10 | 1 | 2 | 1 | 2 |
| 11 | 1 | 2 | 2 | 1 |
| 12 | 2 | 2 | 2 | 1 |
| 13 | 2 | 2 | 1 | 2 |
| 14 | 2 | 1 | 2 | 2 |
| 15 | 1 | 2 | 2 | 2 |

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of manufacturing a chitosan composition comprising steps performed in the following specific order:
   (i) preparing materials including: a microorganism solution, a fruit vinegar, an enzyme solution, and a rice alcohol has alcohol range 30%-50%;
   in which, prepare the microorganism solution by performing steps (A) to (E):
   (A) creating a first suspension solution comprising performing in a specific order from (a1) to (c1):
      (a1) activating *Bacillus* sp. TV11 on the Nutrient agar medium, incubating at 37° C. for a period of 36-48 hours to obtain an activated *Bacillus* sp. TV11;
      (b1) inoculating a single colony of the activated *Bacillus* sp. TV11 into a test tube containing 10 ml of Nutrient broth medium, shaking at 200 rpm for 24 hours at 37° C. to obtain an increased first biomass solution; and
      (c1) inoculating the increased first biomass solution into Nutrient broth medium at a ratio of (1-3): 100, shaking at 200 rpm for 24 hours at 37° C. to obtain the first suspension solution;
   (B) creating a second suspension solution comprising performing in a specific order from (a2) to (c2):
      (a2) activating *Lactobacillus* sp. T432 on the Man Rogosa Sharpe (MRS) agar medium, incubating at 37° C. for a period of 36-48 hours to obtain an activated *Lactobacillus* sp. T432;

(b2) inoculating a single colony of the activated *Lactobacillus* sp. T432 into a test tube containing 10 ml of MRS broth medium, shaking at 200 rpm for 24 hours at 37° C. to obtain an increased second biomass solution; and (c2) inoculating the increased second biomass solution into MRS broth medium at a ratio of (1-3): 100, shaking at 200 rpm for 24 hours at 37° C. to obtain the second suspension solution;

(C) creating a third suspension solution comprising performing in a specific order from (a3) to (c3):

(a3) activating *Lactobacillus plantarum* VTCC 431 on the MRS agar medium, incubating at 37° C. for a period of 36-48 hours to obtain an activated *Lactobacillus plantarum* VTCC 431;

(b3) inoculating a single colony of the activated *Lactobacillus plantarum* VTCC 431 into a test tube containing 10 ml of MRS broth medium, shaking at 200 rpm for 24 hours at 37° C. to obtain an increased third biomass solution; and (c3) inoculating the increased third biomass solution into MRS broth medium at a ratio of (1-3): 100, shaking at 200 rpm for 24 hours at 37° C. to obtain the third suspension solution;

(D) creating a fourth suspension solution comprising performing in a specific order from (a4) to (c4):

(a4) activating *Lactobacillus bulgaricus* VTCC 703 on the MRS agar medium, incubating at 37° C. for a period of 36-48 hours to obtain an activated *Lactobacillus bulgaricus* VTCC 703;

(b4) inoculating a single colony of the activated *Lactobacillus bulgaricus* VTCC 703 into a test tube containing 10 ml of MRS broth medium, shaking at 200 rpm for 24 hours at 37° C. to obtain an increased fourth biomass solution; and (c4) inoculating the increased fourth biomass solution into MRS broth medium at a ratio of (1-3): 100, shaking at 200 rpm for 24 hours at 37° C. to obtain the fourth suspension solution;

(E) mixing (1-2) parts of the first suspension solution with (1-2) parts of the second suspension solution, (1-2) parts of the third suspension solution, and (1-2) parts of the fourth suspension solution to obtain the microorganism solution;

in which, prepare the fruit vinegar by performing steps from (A') to (G') including:

(A') selecting and preparing fruits by a predetermined quality guideline, includes selecting said fruits that have a Brix level of at highest 2; in which fruits are selected from the group consisting of ambarella (*Spondias dulcis*), plum (*Prunus salicina*), apricot (*Prunus armeniaca* (L.)), crocodile fruit (*Dracontomelon duperreanum*), star gooseberry (*Phyllanthus acidus* (L.)), and a combination thereof;

(B') performing visual inspection to select undamaged fruits;

(C') washing fruits, then cold-squeezing fruits to obtain a fruit juice;

(D') creating a foundation solution by mixing the fruit juice and the coconut water in ratio of 1:3;

(E') pasteurizing the foundation solution at 85° C. for 4 minutes, then let it cool, and adjusting the Brix to 6 to obtain a pasteurized solution;

(F') adding ethanol 95% at a ratio of 3% (v/v) to the pasteurized solution, adjusting the pH to 5 by acetic acid 1.5%, then adding *Acetobacter aceti* bacteria in ratio of 1.2% (v/v), and fermenting for 7 days to obtain a solution after fermentation; and (G') filtering the solution after fermentation to obtain the fruit vinegar;

in which, prepare the enzyme solution by performing steps from (A") to (B") including:

(A") creating an enzyme preparation by homogeneously mixing (1-3) parts of a protease ingredient with 1 part of a lipase ingredient; and (B") creating the enzyme solution by homogeneously mixing (3-5) parts of the enzyme preparation with (5000-10000) parts of the water;

in which, prepare the rice alcohol has alcohol range 30%-50% by fermenting a homogeneous mixture twice, then distilling and aging the alcohol using an alcohol aged machine or alcohol aging equipment;

wherein the homogeneous mixture includes 600 parts of a cooked rice mixture, and (1-2) parts of a wine yeast ingredient;

the cooked rice mixture is cooked from 3 parts glutinous rice with 1 part plain rice, 0.2 part shelled green beans, and 4.5 parts water;

wherein the wine yeast ingredient includes 11 parts of a rice flour, (0.6-0.8) parts of an extracted herbal, and (0.001-0.1) parts of a yeast ingredient;

the extracted herbal is extracted from a herbal mixture crushed/chopped, and soaked in solvent, or saturated brine solution; the herbal mixture comprising: *Myristica fragrans* Houtt., *Curcuma aromatica* Salisb., *Atractylodes macrocephala* Koidz., *Mentha arvensis* L., *Amomum aromaticum* Roxb., *Glycyrrhiza uralensis* Fisch., *Foeniculum vulgare* Mill., *Illicium verum* Hook. f., and Cortex *Cinnamomi cassiae*;

the yeast ingredient is listed in Table 3;

(ii) creating a chitin ingredient from shrimp shells comprising performing in a specific order from (a) to (c):

(a) collecting a molting shell of shrimp, then washing to remove impurities, and soaking with HCl solution in a ratio of 1: (3-5) (w/v) for 15-20 days, then filtering to remove liquid, washing twice with the rice alcohol has alcohol range 30%-50 to obtain a first temporary mixture;

(b) treating the first temporary mixture to obtain a basic solution including:

dissolving a quicklime (CaO) ingredient in solution concentrated HCl contains 40% (concentrated grade) with combined stirring at 50 rpm for 5 minutes to obtain a solution 1;

admixing the first temporary mixture to the solution 1 with combined stirring at 50 rpm for 5 minutes, then stop stirring and let stand for 7-10 days at 28° C.-40° C. to obtain the basic solution;

wherein a ratio of the first temporary mixture and the quicklime (CaO) ingredient is 1: (2-5) (w/w);

wherein a ratio of the quicklime (CaO) ingredient and the solution concentrated HCl contains 40% (concentrated grade) is 1: (2-5) (w/v);

(c) admixing 1 part of the enzyme solution at step (i) into 10 parts of the basic solution, then stop stirring and let stand for 12-18 hours to obtain the chitin ingredient from shrimp shells;

(iii) creating a chitin ingredient from oyster mushroom comprising performing in a specific order from (a') to (d'):

(a') collecting oyster mushrooms, then washing to remove impurities, and soaking with the fruit vinegar at step (i) in a ratio of 1: (3-5) (w/v) for 15-20 days, then filtering to remove liquid, and washing twice with the rice alcohol has alcohol range 30%-50% to obtain a second temporary mixture; wherein the fruit vinegar has a concentration of 35%-55%;

(b') treating the second temporary mixture to obtain a basic temporary solution including:

dissolving the quicklime (CaO) ingredient in solution concentrated HCl contains 40% (concentrated grade) with combined stirring at 50 rpm for 5 minutes to obtain the solution 1;

admixing the second temporary mixture to the solution 1 with combined stirring at 50 rpm for 5 minutes, then stop stirring and let stand for 7-10 days at 28° C.-40° C. to obtain the basic temporary solution;

wherein a ratio of the second temporary mixture and the quicklime (CaO) ingredient is 1: (3-5) (w/w);

wherein the ratio of the quicklime (CaO) ingredient and the solution concentrated HCl contains 40% (concentrated grade) is 1: (2-5) (w/v);

(c') admixing the microorganism solution at step (i) into the basic temporary solution at a ratio of (1-2): 10 (w/v) to obtain a foundation temporary solution; and (d') adjusting pH of the foundation temporary solution reached 6.8-7.2, then fermenting at 30° C.-40° C. for 125-135 hours to obtain the chitin temporary mixture from oyster mushroom;

(iv) creating a chitin mixture by homogenously mixing (1-10) parts of the chitin ingredient from shrimp shells at step (ii) with 1 part of the chitin ingredient from oyster mushroom at step (iii);

(v) loading the chitin mixture into the centrifugal spray drying device having predetermined specifications to create the chitosan composition;

in which predetermined specifications including: a rotate speed of 1200 rpm for 3-5 hours at temperature 20° C.-28° C.; and (vi) packaging and preservation.

2. The method of claim 1, wherein characterized in that the washing temperature of the distilled water is 55° C.-60° C.

3. The method of claim 1, wherein the molting shell of shrimp is a molting shell of shrimp from 60-180 days old shrimp.

4. The method of claim 3, wherein the molting shell of shrimp is the molting shell of shrimp from 61-90 days old shrimp.

5. The method of claim 4, wherein the molting shell of shrimp is the molting shell of shrimp from 71-80 days old shrimp.

6. The method of claim 1, wherein the molting shell of shrimp is selected from the group consisting of litopenaeus vannamei (*Penaeus vannamei*), *Penaeus monodon, Penaeus Merguiensis, Macrobrachium rosenbergii, Metapenaeus ensis, Macrobrachium lanchesteri, Fenneropenaeus Merguiensis, Penaeus Semisulcatus*, and a combination thereof.

7. The method of claim 1, wherein the rice alcohol has alcohol range 45%-50%.

8. The method of claim 1, wherein oyster mushrooms are selected from the group consisting of *Pleurotus pulmonarius, Pleurotus* cf. *floridanus, Pleurotus ostreatus, Pleurotus citrinopileutus*, and a combination thereof.

9. The method of claim 1, wherein the wine yeast ingredient includes 11 parts of the rice flour, (0.6-0.8) parts of the extracted herbal, and (0.01-0.1) parts of the yeast ingredient.

10. The method of claim 9, wherein the wine yeast ingredient includes 11 parts of the rice flour, 0.7 parts of the extracted herbal, and (0.01-0.1) parts of the yeast ingredient.

11. The method of claim 1, wherein at step (ii) the ratio of the first temporary mixture and the quicklime (CaO) ingredient is 1:3 (w/w).

12. The method of claim 1, wherein at step (iii) the ratio of the second temporary mixture and the quicklime (CaO) ingredient is 1:4 (w/w).

13. The method of claim 1, wherein at step (iv) mixing (1-7) parts of the chitin ingredient from shrimp shells with 1 part of the chitin ingredient from oyster mushroom obtain to the chitin mixture.

14. The method of claim 13, wherein at step (iv) mixing (1-5) parts of the chitin ingredient from shrimp shells with 1 part of the chitin ingredient from oyster mushroom obtain to the chitin mixture.

15. The method of claim 14, wherein at step (iv) mixing (1-3) parts of the chitin ingredient from shrimp shells with 1 part of the chitin ingredient from oyster mushroom obtain to the chitin mixture.

16. The method of claim 1, wherein at step (v) time is 5 hours.

17. The method of claim 1, wherein the method further comprising a step drying the chitosan composition at 70° C. for 5-10 minutes before the step (vi) packaging and preservation.

18. The method of claim 1, wherein at step (v) temperature is 25° C.

19. The method of claim 1, wherein at step (v) the chitosan composition has a pH of 7-8.5.

20. The method of claim 19, wherein at step (v) the chitosan composition has a pH of 8-8.5.

* * * * *